(12) United States Patent
    Jacobsson et al.

(10) Patent No.: US 9,107,764 B2
(45) Date of Patent: Aug. 18, 2015

(54) MEDICAL CLOSURE DEVICE

(75) Inventors: Christer Jacobsson, Taby (SE); Martin Johansson, Valla (SE); Jimmy Gido Schon, Jonkoping (SE); Jens Nygarden Brandstorm, Jonkoping (SE); Janame Wetterheim, Bankeryd (SE); Erik Elwing, Jonkoping (SE)

(73) Assignee: Ostomycure AS, Oslo (NO)

( * ) Notice: Subject to any disclaimer, the term of this patent is extended or adjusted under 35 U.S.C. 154(b) by 542 days.

(21) Appl. No.: 13/499,621

(22) PCT Filed: Oct. 1, 2010

(86) PCT No.: PCT/GB2010/001846
    § 371 (c)(1),
    (2), (4) Date: Jun. 8, 2012

(87) PCT Pub. No.: WO2011/039517
    PCT Pub. Date: Apr. 7, 2011

(65) Prior Publication Data
    US 2012/0245535 A1     Sep. 27, 2012

(30) Foreign Application Priority Data
    Oct. 1, 2009  (EP) .................................... 09171963

(51) Int. Cl.
    *A61F 5/44*      (2006.01)
    *A61F 5/445*     (2006.01)
    *A61F 5/448*     (2006.01)

(52) U.S. Cl.
    CPC ......... *A61F 5/445* (2013.01); *A61F 2005/4455* (2013.01); *A61F 2005/4486* (2013.01)

(58) Field of Classification Search
    USPC .................................................. 604/342, 332
    See application file for complete search history.

(56) References Cited

U.S. PATENT DOCUMENTS

| 2,585,716 | A | * | 2/1952 | Zaetz | 604/342 |
|-----------|---|---|--------|-------|---------|
| 3,557,790 | A |   | 1/1971 | Hauser | 128/283 |
| 4,460,363 | A | * | 7/1984 | Steer et al. | 604/336 |
| 4,534,768 | A | * | 8/1985 | Osburn et al. | 604/350 |
| 4,592,750 | A | * | 6/1986 | Kay | 604/337 |

(Continued)

FOREIGN PATENT DOCUMENTS

| EP | 0 461 007 A1 | 12/1991 |
|----|--------------|---------|
| EP | 0 463 359 B1 | 1/1992 |

(Continued)

OTHER PUBLICATIONS

International Search Report, PCT/GB2010/001846, Jan. 27, 2011.

*Primary Examiner* — Tatyana Zalukaeva
*Assistant Examiner* — Guy K Townsend
(74) *Attorney, Agent, or Firm* — Winston & Strawn LLP

(57) ABSTRACT

A medical closure device serves for coupling to a discharge opening of a device protruding from a mammalian body. The medical closure device includes a coupling part for engaging a part of the device protruding from the mammalian body. The coupling part is a circumferential flexible member delimiting a coupling opening configurable between a relaxed configuration where the coupling opening cannot pass over the medical device and a stressed configuration where the coupling opening of the coupling part can pass over the medical device. The coupling part has a securing member for securing the coupling part to a closure part, such as a cap, an ostomy bag, a catheter, or an irrigation device, for subsequent closure of a discharge opening.

30 Claims, 6 Drawing Sheets

(56) References Cited

U.S. PATENT DOCUMENTS

| | | | |
|---|---|---|---|
| 4,973,323 A * | 11/1990 | Kaczmarek et al. | 604/339 |
| 5,041,102 A * | 8/1991 | Steer et al. | 604/338 |
| 5,088,992 A | 2/1992 | Edwards et al. | 604/338 |
| 5,163,930 A * | 11/1992 | Blum | 604/338 |
| 5,411,491 A * | 5/1995 | Goldhardt et al. | 604/247 |
| 5,607,413 A * | 3/1997 | Holmberg et al. | 604/342 |
| 5,647,861 A * | 7/1997 | Steer et al. | 604/342 |
| 5,662,628 A | 9/1997 | Hollands | 604/342 |
| 6,537,261 B1 | 3/2003 | Steer et al. | 604/342 |
| 8,142,406 B2 * | 3/2012 | Blum | 604/338 |
| 8,211,073 B2 * | 7/2012 | Dove et al. | 604/342 |
| 2004/0193122 A1 * | 9/2004 | Cline et al. | 604/332 |
| 2005/0143696 A1 * | 6/2005 | Pedersen et al. | 604/332 |
| 2007/0088300 A1 * | 4/2007 | Cline et al. | 604/342 |
| 2007/0129695 A1 * | 6/2007 | Blum | 604/338 |
| 2009/0118687 A1 | 5/2009 | Kristensen et al. | 604/342 |
| 2009/0157140 A1 * | 6/2009 | Martino et al. | 607/41 |
| 2009/0163886 A1 * | 6/2009 | Therkelsen et al. | 604/342 |
| 2012/0123361 A1 * | 5/2012 | Johansson et al. | 604/337 |
| 2012/0245535 A1 * | 9/2012 | Jacobsson et al. | 604/264 |

FOREIGN PATENT DOCUMENTS

| | | |
|---|---|---|
| EP | 0 737 458 A2 | 10/1996 |
| EP | 1 013 250 A1 | 6/2000 |
| EP | 1 550 422 A2 | 7/2005 |
| GB | 2 340 756 | 3/2000 |
| WO | WO 02/09629 A1 | 2/2002 |
| WO | WO 2007/059774 A2 | 5/2007 |

* cited by examiner

MEDICAL CLOSURE DEVICE

This application is a 371 filing of International Patent Application PCT/GB2010/001846 filed Oct. 1, 2010.

BACKGROUND

The invention relates to a medical closure device adapted for coupling to a discharge opening of a medical device protruding from a mammalian body, which closure device comprises a coupling part for engaging the part of the device protruding from the mammalian body.

Within the scope of the present invention the term "medical closure device" means any device that can close, or cooperate with further components to close, a discharge or supply opening to prevent discharge or spillage. Thus a "medical closure device" provides, or facilitates the provision of, a boundary to the environment to terminate and shut off access to the body. "Medical closure devices" may include bags and pouches.

The medical device could for example be an implant, providing an external opening to achieve temporary or permanent access to and/or communication with a body vessel or a body cavity, a catheter, a tracheal port, or an infusion port.

In particular the medical device could be an implant associated with an ostomy, i.e. a surgically created opening between the small bowel or large bowel and the skin of the abdomen, i.e an ileostomy or a colostomy, respectively, through which stool and gas are passed. Similarly an urostomy may be created for discharging urine. However, irrespective of the kind of discharged matter, discharging must be made in a controlled way and body waste matter needs to be stored either in an internal reservoir or in an external reservoir until final disposal. The associated implants serve in particular for securing pouches for collecting continuous, uncontrolled discharge of body waste, or for temporary closure of an internal continent reservoir to be evacuated or irrigated optionally by the patients interaction when appropriate and convenient for the patient. Antegrade irrigation may take place by instilling water or other kinds of enemas through specialised equipment through the stoma to control stoma output. Faeces evacuates by reflexive peristaltic enabling the patient to control the stoma action to a certain degree, unlike the patient whose stoma spontaneously evacuates and needs to wear an appliance. In the intervals between evacuations, stomas and/or some internal continent reservoirs necessitate leakproof closure for preventing spontaneous evacuation.

A gastrostomy, i.e. an artificial external opening into the stomach, may e.g. be provided for nutritional support.

Known medical cap means or medical closure devices for sealing closures of ostomy implants are difficult to operate and are often customised to a specific implant. Moreover, such medical cap means or medical closure devices may be difficult to operate in relation to the ostomy implant because the stoma site can be difficult for the patient to view. Moreover, operation of the medical cap means or medical closure means involves a risk of injuring the sensitive tissue attachment between body and ostomy implant during multiple fastenings and removals of medical cap or medical closure device, irrigation device and/or coupling flange of ostomy bag.

Also in relation to other medical devices inserted for obtaining temporary access to a cavity or vessel inside the body, e.g. a catheter, a tracheal port, or an infusion port, the selection of medical cap means or closure means that can be substituted or opened and closed multiple times in a reliable and sealing manner without injuring or irritating the body are limited.

WO 02/09629 discloses a clamp for mounting e.g. an ostomy pouch on an implant. The clamp is formed from a ring with a slit in it. An arm is attached to the ring on either side of the slit and by squeezing/releasing the arms the ring is caused to expand/contract so that it can be attached to the implant. However, this arrangement is not robust and may be inconvenient for the patient to operate.

Thus there is a demand for new medical closure devices for medical devices implanted or inserted into the mammalian body and it would be desirable to provide a medical closure device of the kind mentioned in the opening paragraph, which medical closure device can be operated numerous times without injuring or irritating the tissue attachment of the device to the mammalian body.

SUMMARY OF THE INVENTION

According to a first aspect, the present invention provides a medical closure device adapted for coupling to a discharge opening of a device protruding from a mammalian body, which medical closure device comprises a coupling part for engaging a part of the device protruding from the mammalian body, wherein the coupling part is a circumferential flexible member delimiting a coupling opening configurable between a relaxed configuration where the coupling opening cannot pass over the medical device and a stressed configuration where the coupling opening of the coupling part can pass over the medical device.

Thus the medical closure device of the invention provides a convenient means by which the device protruding from a mammalian body can be closed. Preferably the closure device further comprises or is adapted to be connected to a closure part that completes the closure, e.g. a lid or cap. Alternatively, the closure part may be formed integrally with the medical closure device. Thus the closure device may form the entire closure or be part of a closure. As such, in some embodiments the closure device of the present invention may be seen as an adapter or coupling part for connecting a closure part to a device protruding from a mammalian body.

Preferably the coupling part is continuous, e.g. a closed ring. No slit or other gap is provided in the coupling part that breaks the ring. Moreover in the present invention, the coupling part preferably deforms, e.g. changes shape, when being altered from the relaxed to the stressed configuration. This is in contrast to WO 02/09629 in which the shape of the clamp does not change when being attached/removed: it remains a circular shape.

Thus preferably the coupling part is deformable between the relaxed and stressed configurations. Preferably it is radially deformable, e.g. the circumferential member of the coupling part deforms in a radial direction in order to change between the relaxed and stressed configurations. Preferably the coupling part is deformable between the relaxed configuration and the stressed configuration by the application of pressure to the coupling part, preferably on opposite sides of the coupling part. Thus the coupling part is preferably arranged such that if it is squeezed, it will deform from the relaxed to the stressed configuration, enabling it to be passed over the protruding device. When pressure is released, the coupling part will attempt to return to the relaxed configuration, thus gripping the protruding device. It can be removed by again squeezing the coupling part to deform it to the stressed configuration, removing it from the protruding device and releasing it.

Thus according to another aspect, the present invention provides a medical closure device adapted for coupling to a discharge opening of a device protruding from a mammalian body, wherein the medical closure device comprises a coupling part for engaging a part of the device protruding from the mammalian body, and wherein the coupling part comprises a circumferential deformable member delimiting a coupling opening, and wherein the shape of the coupling part can be deformed by applying pressure to one or more sides of the coupling part, preferably on opposite sides, so that the coupling part can be arranged over the device.

In another aspect the invention provides a closure adaptor for coupling to a discharge opening of a device protruding from a mammalian body, wherein the closure adaptor is arranged to be squeezed, preferably on opposite sides, in order to change the shape of the closure adaptor such that it can be fitted over the device protruding from a mammalian body. Preferably the closure adaptor is arranged such that when the squeezing force is released, the closure adaptor grips the device.

Preferably the coupling part/closure adaptor comprises surfaces for applying pressure/squeezing by a user in order to deform the shape of the coupling part/closure adaptor.

Due to the flexibility of the circumferential flexible member, the coupling part can be deformed so that the shape and size of the coupling opening is altered by application of stress, resulting in that the coupling part can be easily snapped on the medical device almost by itself. Once the stress is relieved the coupling part will revert towards the relaxed configuration as far as the size, design and outline of the medical device allows for it. Thus the coupling opening is easy to mount to and demount from the medical device protruding from the mammalian body. By carefully selecting, amongst others, features such as the dimensions and the size of the coupling opening, the nature of the material of the coupling part and/or the structure of the flexible member, it is achieved that one coupling part fits numerous devices.

Accordingly, a device need not be specifically adapted for securing of the coupling part although suitable mating means on the medical device may be provided on the exterior side of the medical device for securing purposes. The medical device may have a circumferential breast, which the coupling opening can be stressed to pass over, to be arranged below in a substantially relaxed condition abutting the medical device. The high degree of configurability between the relaxed and the stressed configuration ensures reliable engagement with the medical device, either by engaging mating means on the medical device or simply by frictional engagement. When the coupling part is mounted on the medical device the flexible member reverts at least partly to the relaxed position after having been stressed, but can also revert entirely to the relaxed configuration.

In the preferred embodiment the coupling opening of the coupling part has a semi-minor axis that is smaller than a semi-major axis in the relaxed configuration. Wherein, said semi-minor axis, in the relaxed configuration of the coupling part prior to passing the coupling opening over the medical device, is smaller than or equal to the exterior radius of the medical device to be surrounded by the coupling opening. Thus the coupling opening of the coupling part is substantially oval, elliptical or semi-elliptical in the relaxed configuration, but can be altered by application of stress to a more circular shape to enabling mounting of the device. When the stress is relieved, reverting at least partly to the substantially oval shape secures the coupling part onto the device because the coupling part will inherently aim for the relaxed configuration but may be prevented from doing so entirely by the medical device arranged in the coupling opening.

As mentioned above, the shape of the coupling opening may be altered by stress application so that the semi-major axis of the coupling opening of the coupling part in the stressed configuration can be made either smaller than in the relaxed configuration of the coupling part, equal to or smaller than the semi-minor axis in the relaxed configuration, or smaller than the semi-minor axis in the stressed configuration whereby the coupling part almost automatically clamps onto the device once stress is relieved.

This can be achieved either by compressing the coupling ring in a single plane perpendicular to the axis of the coupling opening or by partly bending or folding the coupling part out of said plane or by a combination of compressing and bending.

In an application where a certain position of the coupling part is required for mounting onto the medical device and/or a high degree of sealing is required, the coupling part may be provided with engagement means for engaging the medical device. Such engagement means may function in a manner similar to a key and slot preventing the coupling part from taking other annular and axial positions than the optimum. When the coupling part is relaxed, the engagement means may by itself enter into engagement with corresponding engagement means on the exterior circumferential side of the device. The substantially oval shape contributes to the correct self-orientation of the coupling part that enables proper engagement between coupling part and medical device. If e.g. the medical closure device is an ileostomy bag intended for bottom discharge, the ileostomy bag needs to be oriented with the discharge opening facing downwards. To this aspect the engagement means may serve as an expedient orientation guide means that automatically facilitates a correct and tight arrangement of the ileostomy bag on the ostomy implant using the oval snap-on coupling part according to an embodiment of the present invention.

In a preferred embodiment, the coupling part may also have securing means for securing the coupling part to a closure part. The coupling part may e.g. have a coaxially protruding part with an external thread for threading with a corresponding internal thread on a closure part in the form of a cap or lid means. Alternatively, the coupling part may have one or more coaxially protruding webs or hooks to be secured in complementary shaped openings on the medical closure part. A vice versa arrangement, complementarily shaped snap-fitting flanges, key and slot means or similar securing and coupling means on opposite facing parts of the coupling part and the closure part are also provided according to embodiments of the present invention.

In one embodiment, the coupling means and closure part are arranged such that when they are interconnected, the coupling means is locked in a particular configuration. Preferably, the coupling means and closure part are arranged such that when the coupling means is mounted on the medical device, securing the closure part of the coupling means locks the coupling means in position. For example, the securing means of the coupling means may attach to the closure part in such a way that the coupling means is prevented from subsequently deforming.

Thus, when mounted on the medical device, the coupling part is prevented from being deformed to a stressed configuration which would allow it to be removed. The interconnection between the coupling means and the closure part may be rigid. For example if the interconnection is by means of a screw thread, when the closure part is screwed onto the coupling means, the coupling means is retained in the configuration set by the rigid interconnection, so cannot be deformed and removed from a medical device on which it is mounted, until the closure part is removed.

To prevent leakage of fluid between the medical device and closure device in the assembled state, the medical closure device may advantageously comprise a sealing means for sealing towards the medical device. In one embodiment the sealing means is a sealing ring. The sealing ring may be a gasket, packing, or other kind of seal suitable for tightening between the medical device and the components of the medical closure device. One or more sealing rings may also be provided. In an alternative embodiment, the sealing means comprises a sealing disc. The sealing disc is preferably injection moulded together with the closure part.

If the circumferential flexible member forming the coupling part has at least one aperture, through-opening or cut-out, the structure of the coupling ring can be made even more flexible, expensive materials are saved, and the open-structured coupling part serves for making the medical closure device lightweight. Thus hole(s), aperture(s), through-opening(s) or cut-out(s) having a through-going axis parallel to the axis of the coupling opening provides in a synergistic manner not only an inexpensive coupling part but also a coupling part with a high degree of resiliency and flexibility, that enhances user-friendliness and makes the medical closure device easy to handle.

In a preferred embodiment, the coupling part has first grip means for at least operating the coupling part during attachment to and detachment from the closure part, and/or the coupling part has second grip means for at least gripping the coupling part during configuration of the coupling opening between the relaxed configuration and the stressed configuration and vice versa. The second grip means enables the patient to very easily identify the relaxed configuration of the coupling part and make the necessary application of force to transfer the coupling part to the stressed configuration. Thus the second grip means enables the patient to grasp the coupling part with the fingers in the correct orientation for configuration from relaxed to stressed condition of the coupling part. The first grip means is provided with another design or is of another kind than the second grip means so that the patient is able to distinguish between the first grip means and the second grip means and to prevent e.g. unintentional detachment of the coupling part from the medical device when the intention is to instead disengage the coupling part and the closure part. Thus the first grip means and second grip means enhances user-friendliness and enables the patient to handle the coupling part of the medical closure device without mistake and accidental disengagement of closure part, coupling part and medical device.

Preferably the first grip means can be arranged along the semi-minor axis and the second grip means arranged along the semi-major axis so that the compression and deformation of the coupling opening to open said coupling opening takes place as intended along the semi-major axis, and not along the semi-minor axis. Moreover, operating the first grip means does not noticeably affect the shape and size of the coupling opening when the first grip means are arranged along the semi-minor axis and there is therefore no risk that the coupling part gets detached from the medical device when the closure part is to be removed from the coupling part.

In an advantageous embodiment, the closure part may be provided with third grip means for gripping the closure part during attachment of the closure part and the coupling part, and during detachment of the closure part from the coupling part, optionally during screwing and unscrewing the closure part and the coupling part, optionally during snap-fitting or snap-fastening the closure part and the coupling part and reversing the snap-fitting and the snap-fastening. The third grip means enables the patient to get a good grip on the closure part and to counteract and neutralize forces applied to the medical device when the patient needs detachment of the closure part to get access to the body cavity or vessel, e.g. when an internal continent reservoir needs evacuation. In this case the second grip means is held with the fingers of one hand, to ensure that the medical device remains firmly where it is implanted or inserted, while the third grip means is taken and operated with the fingers of the opposite hand to facilitate removal of the closure part without serious dislocation of any of the coupling part or the medical device.

If the closure part has a concavity for accommodating at least a part of the coupling part and a part of the medical device protruding from a mammalian body, there is less protrusion of the medical closure part from the mammalian body thus reducing/avoiding disfiguring the appearance of the patient.

In the preferred embodiment at least one of the coupling part or the closure part is made of a flexible material having memory shape, or has memory shape due to structural design, or combinations of both. Any of said parts may e.g. be manufactured of resilient polymeric materials having the ability to return from a temporarily deformed shape state, the stressed configuration induced by application of an external force, to an original, permanent shape, the relaxed configuration. Suitable materials having a high degree of memory shape include e.g. natural and synthetic rubbers which also may be elastic. The memory shape may also be provided due to structural design in which case e.g. the at least one aperture, through-opening or cut-out of the flexible circumferential member forming the coupling part provide for a corresponding memory in that these openings are inclined to self-erect when relieved subsequent to compression of the coupling part.

In both embodiments the circumferential flexible member is an uninterrupted, closed oval ring. Thus, the overall length of the perimeter of the annular member remains substantially the same in any configuration, irrespective of deformation of the coupling opening of the circumferential member, except for a possible minimal elongation due to any inherent elastic properties of selected manufacturing materials. In both embodiments, the deformation between relaxed and stressed configurations is fully reversible.

The medical closure part may be selected from the group comprising a cap, an ostomy bag, a catheter, or an irrigation device, such as an antegrade irrigation device. It may also form an adapter, connector or coupling part for such components.

Preferably, the closure part has rounded edges to prevent scratching the patient's skin.

The invention also relates to a method for application of the medical closure device described and discussed above onto a device protruding from a mammalian body.

According to the a second aspect, the present invention provides a method for application of a closure device as described above onto a medical device protruding from a mammalian body, the method comprising the steps of:
  increasing the length of the semi-minor axis by applying an exterior force to the coupling part to allow the coupling opening to pass over a part of a medical device protruding from the mammalian body,
  arranging the coupling part to surround the protruding part of the medical device,
  relaxing the exterior force allowing the coupling part to revert at least partly to the relaxed configuration, and
  arranging the closure part on the coupling part for subsequent closure of the medical device protruding from a mammalian body.

If the coupling part and the closure part are provided with external and internal threading said parts may be screwed together for end-closing the discharge opening of the medical device. If alternatively, the coupling part and the closure part are provided with mating complementary coupling flanges or other suitable mating coupling means, the coupling part and the closure part may be snapped or clicked together.

The preferred use of the closure device is for closure of a medical implant, preferably an ostomy implant.

In case that the closure part is a lid, a flexible semi-spherical cap member may serve the lid function. In this embodiment, the coupling ring is from the start arranged inside the concavity of the semi-spherical cap member and the cap member serves as a convenient tool for holding the medical closure device consisting of a coupling part combined with a closure part for changing the configuration of the coupling ring when the medical closure part is to be mounted on the medical device.

The invention also provides a closure part adapted for mounting to a medical closure device as described above.

Preferably, the closure part comprises securing means for securing the closure part to the coupling part of the medical closure device.

The invention further provides a kit comprising a medical closure device as described above and a closure part adapted for mounting to the medical closure device for closing the closure device.

According to yet another aspect, the present invention provides a method of coupling a medical closure device to a discharge opening of a device protruding from a mammalian body, the medical closure device comprising a coupling part for engaging a part of the device protruding from the mammalian body, the coupling part being a circumferential flexible member delimiting a coupling opening, the method comprising the steps of:
- applying force to a coupling part in a relaxed configuration so as to place it in a stressed configuration wherein the coupling opening can pass over the protruding part of the device;
- locating the coupling opening around the protruding part of the device;
- relaxing the force on the coupling part so that it at least partially returns to the relaxed configuration wherein it cannot pass over the protruding part of the device, whereby the medical closure device becomes attached to the device protruding from the mammalian body.

Preferably, in the relaxed configuration the coupling opening is substantially elliptical. Preferably in the stressed configuration the coupling opening is less elliptical than in the relaxed configuration. Preferably in the stressed configuration the coupling opening is substantially circular.

It will be appreciated that, at least in its preferred form, the present invention provides a medical closure device of the kind mentioned in the opening paragraph, which medical closure device can be mounted on medical devices with different external diameters. It further aims to provide a medical closure device of the kind mentioned in the opening paragraph, which medical closure device can be mounted on medical devices with arbitrary exterior perimeters. In addition, it aims to provide a medical closure device of the kind mentioned in the opening paragraph, for temporary closure of an implant associated with an ostomy.

BRIEF DESCRIPTION OF THE DRAWINGS

Preferred embodiments of the present invention are described below by way of example only and with reference to the accompanying drawings. For like parts the same reference numerals are used.

DETAILED DESCRIPTION OF THE INVENTION

Figure 1:
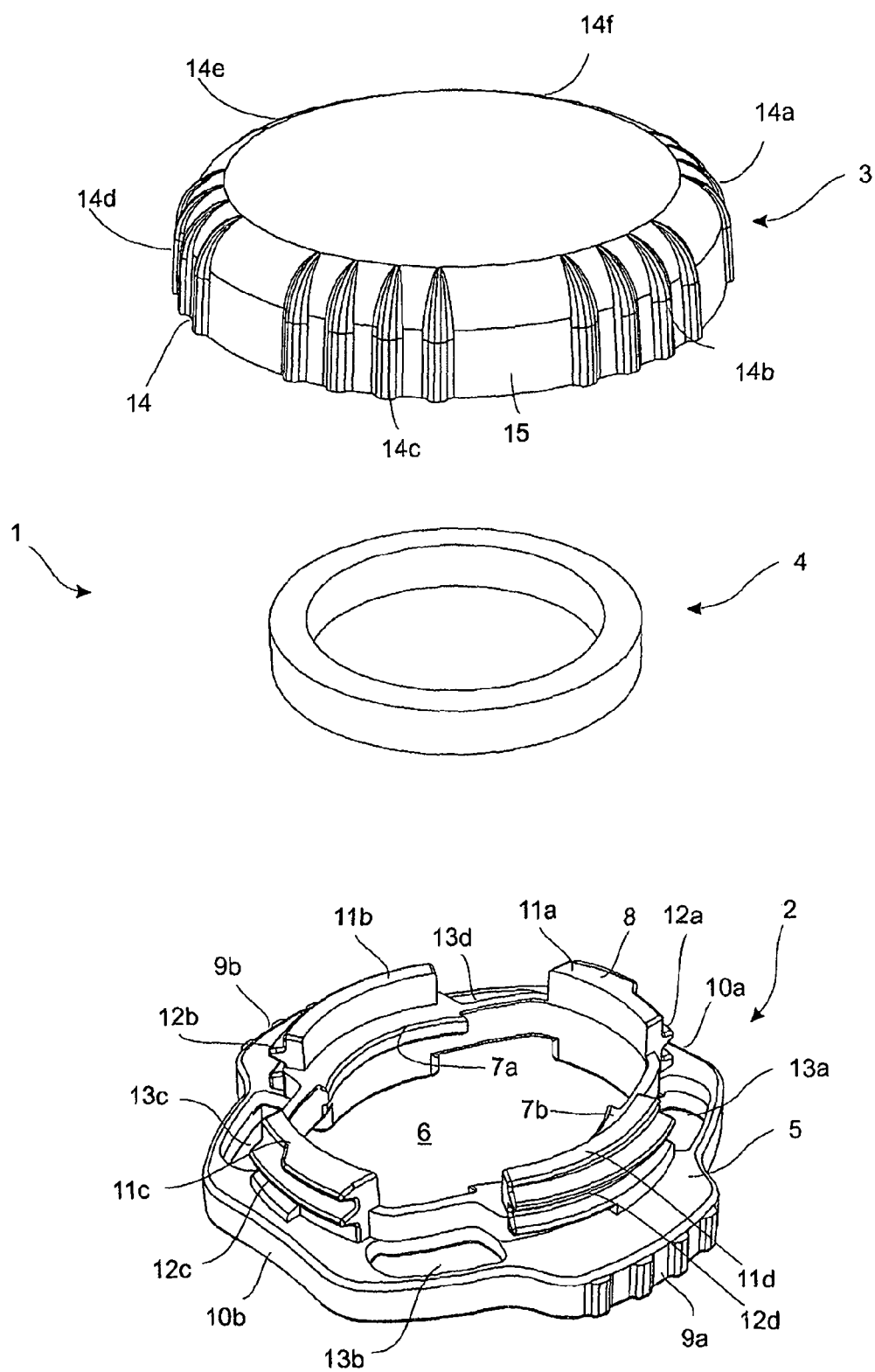
FIG. 1 shows an exploded perspective view of a first embodiment of a medical closure device for closing a discharge opening of an ostomy implant.

The first embodiment 1 of a medical closure device 1 consists of a coupling part 2, a closure part 3, and a sealing ring 4.

The coupling part 2 has a circumferential flexible member 5 with a coupling flange 8 protruding axially towards the closure part 3. The circumferential flexible member 5 delimits a substantially oval coupling opening 6 that can be deformed between the relaxed configuration shown in FIG. 1 and a stressed configuration where the shape of the coupling opening 6 and the circumferential flexible member 5 is changed to facilitate mounting on medical device such as an ostomy implant (not shown). Opposite breasts 7a,7b protrude radially from the circumferential flexible member 5 into the coupling opening 6 to carry the sealing ring 4 when the coupling part 2 and closure part 3 are mutually joined. The sealing ring 4 may be integrated in the closure part 3 or be a separate part to be joined with any of the closure part 3 or the coupling part 2, in which latter case the sealing ring 4 is selected to be configurable in the same manner and degree as the coupling part 2.

The exterior perimeter of the coupling part 2 has two radial opposite protruding first grip means 9a,9b for abutment of the patient fingers when the closure part 3 is mounted on or demounted from the coupling part 2. The first grip means 9a, 9b are ribbed to ensure a reliable grip and avoid accidental loss of grip during handling, and for easy and fast location and identification of the first grip means 9a,9b to avoid mix-up with second grip means 10a,10b located alternately with the first grip means 9a,9b. The second grip means 10a,10b are configured as concave indentations 10a,10b, with a shape substantially complementary to a finger, to facilitate a good grip for the patients fingers when stressing the coupling part 2. A concavity provides an inherent hint to the patient of which direction the coupling opening 6 should be compressed to achieve the stressed configuration of the coupling part 2.

Although the first grip means 9a,9b is intended to be the preferred grip means when the closure part 3 is attached to and detached from the coupling part 2, the second grip means 10a, 10b may be used for this purpose too if such use suits the patient the better. The above given advice of how to use the first grip means 9*a*, 9*b* and second grip means 10*a*, 10*b* is to be seen as a guideline only, and the patient or other operator, such as a nurse, can arbitrarily choose hers/his own best mode of operation. The first grip means 9*a*,9*b* and second grip means 10*a*,10*b* confer a high degree of user-friendliness and freedom to operate the medical closure part 1 according to individual capability and circumstances.

The coupling flange 8 encircles coaxially the coupling opening 6 and includes four protruding webs 11*a*, 11*b*, 11*c*, 11*d* having exterior thread 12*a*,12*b*,12*c*,12*d* for screwing together with the closure part 3. The coupling ring 2 is also penetrated by four apertures 13*a*,13*b*,13*c*,13*d* provided circumferentially between neighbouring first grip means and second grip means. The apertures 13*a*, 13*b*, 13*c*, 13*d* may provide for further radial flexibility of the coupling part 2, serve as breathing apertures for allowing air to access the skin and moisture to leave the skin once the coupling ring 2 is mounted on the medical device attached to the mammalian body, as well as to serve as additional grip means.

The closure part 3 is a lid or cap 3 having a substantially flat exterior side for preventing entangling with clothes etc. The lid 3 has third grip means 14, in the form of six sets of ribs 14*a*, 14*b*,14*c*,14*d*,14*e*,14*f* circumferentially distributed around the circumferential wall 15 of the lid 3. Any number of ribs may be provided and other kinds of tactile identification and holding means are foreseen within the scope of the present invention.

Figure 2:
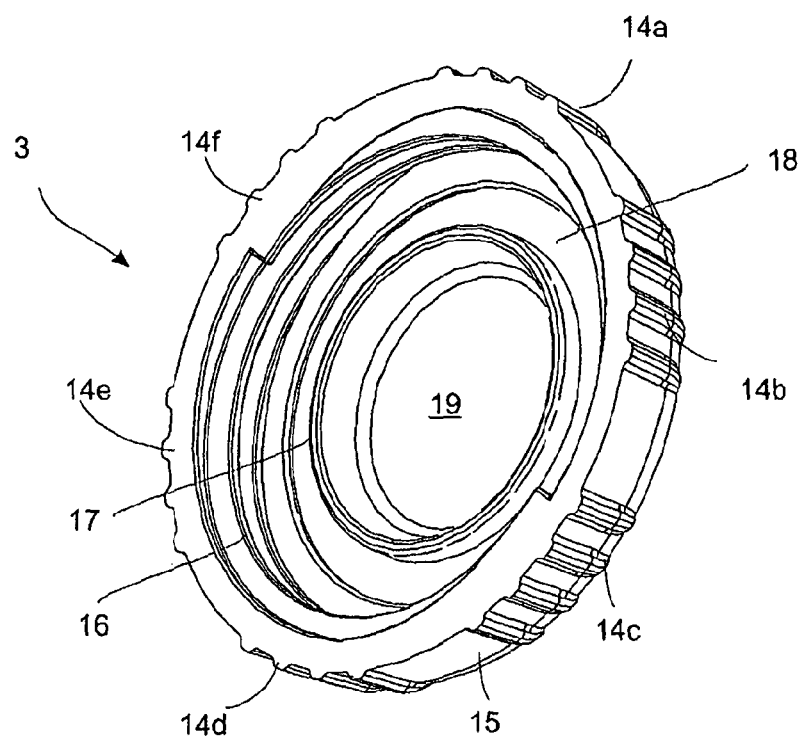
FIG. 2 shows oblique from the side facing the coupling part, a perspective view of the closure part shown in FIG. 1 having an interior thread.

As seen better in FIG. 2 the lid 3 has an internal thread 16 for screwing together with the exterior thread 12*a*,12*b*,12*c*, 12*d* of the coupling part 2 and a circumferential projection 17 for delimiting a recess 18 for accommodation of the sealing ring 4, which sealing ring 4 is to be squeezed to make a fluid-tight seal against a medical device and close the discharge opening of the medical device (not shown) when the medical closure device is mounted on the medical device. The third grip means 14*a*,14*b*,14*c*, 14*d*, 14*e*, 14*f* enables the patient to maintain a grip on the lid 3 when the lid 3 is rotated either clock-wise or counter-clockwise depending on whether the lid 3 is mounted or demounted and whether the threads are right-handed or left-handed. Additionally, the lid 3 substantially hides the coupling part 2, and a part of the medical device inside its cavity 19. Suitable medical devices in the form of implants are disclosed in the applicant's own European patent applications no. EP 04077475.4, EP 07705969.9 or EP 07114671.6 but the use of the medical closure device according to the present invention is not limited to use with these kinds of implants.

Figure 3:
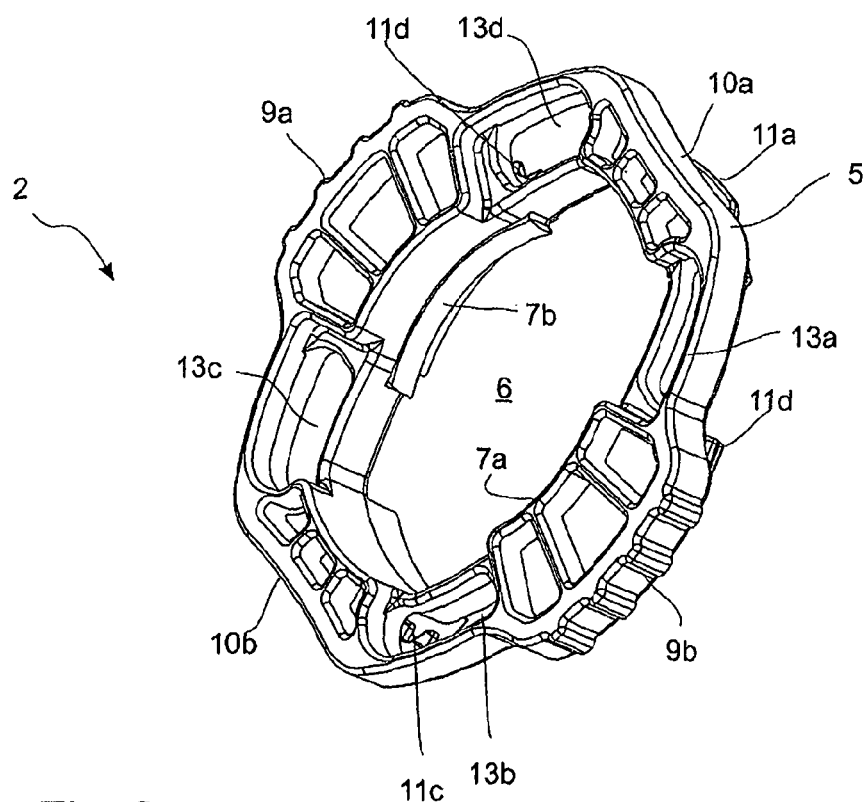
FIG. 3 shows a perspective view of the coupling part shown in FIG. 1 seen from the side facing the body.

FIG. 3 illustrates the coupling part 2 of the first embodiment of a medical closure device 1 seen oblique from the mammalian body facing side. The breasts 7*a*,7*b* protrude radially into the coupling opening 6. A medical device (not shown) can thus be located either just below the breasts 7*a*,7*b*, between the breasts 7*a*,7*b* in the same plane as the breasts 7*a*,7*b*, or a small distance beyond the breasts 7*a*,7*b* into the closure part 3. In all three embodiments the medical device and the closure device 1 may be held firmly engaged by means of the flexibility of the circumferential flexible member 5.

Figure 4:
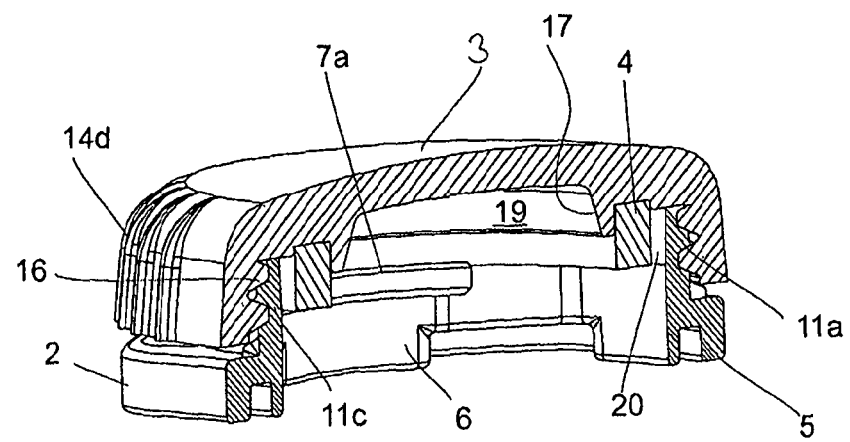
FIG. 4 shows a sectional, axial view taken through the closure device shown in FIG. 1 in the assembled state, where the closure part is screwed onto the coupling part.

An annular wall of a medical device, such as an implant, may be confined in the circumferential gap 20 between the sealing ring 4 and the protruding flange 8 of the coupling part, as seen in FIG. 4, which is a sectional view taken through a closure device in the assembled state. Alternatively the medical device may be mounted so that the sealing ring 4 surrounds a protruding part of the medical device, and the circumferential projection 17 abuts a free end of an annular wall of said tubular protruding part. Once the closure part 3 is secured on the coupling part 2, which has been mounted on the medical device, the sealing ring 4 is compressed both axially and radially to fill out all spaces to create a completely fluid-tight coupling between the medical device and the closure device.

Figure 5:
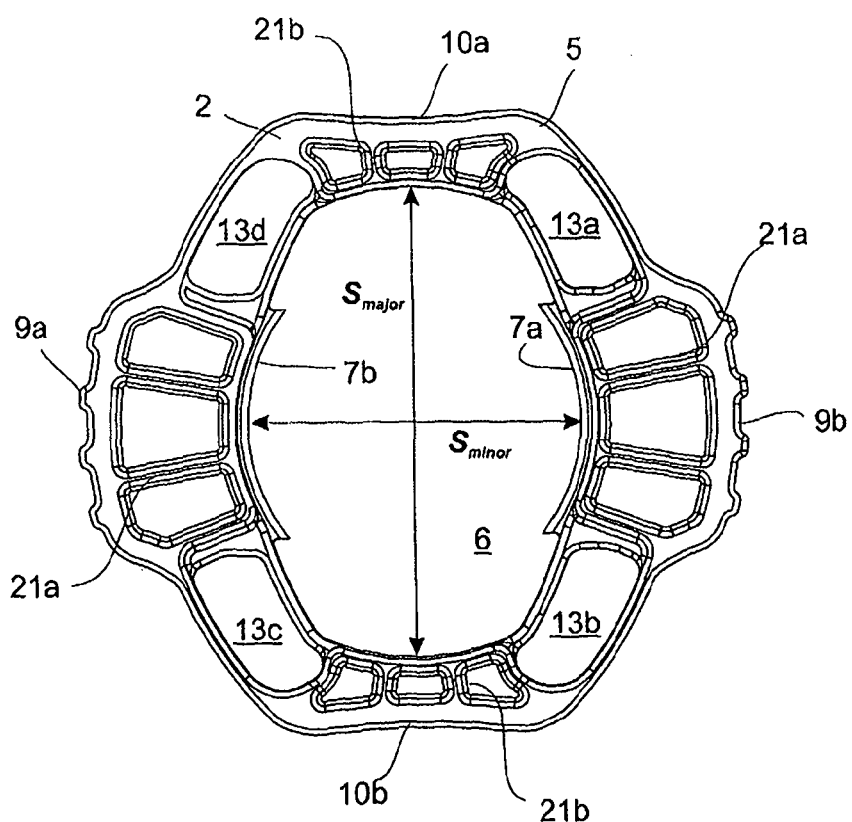
FIG. 5 shows the coupling part seen from the underside facing the medical device and the mammalian body.

FIG. 5 shows the coupling part 2 from below, i.e. the side facing the medical device and the mammalian body. The first grip means 9*a*, 9*b* of the circumferential flexible member 5 is provided with radial crossbars 21*a* to make the first grip means 9*a*, 9*b* partly hollow in order to save material and make the coupling part light-weight. Corresponding hollowness is achieved with respect to the second grip means 10*a*,10*b* and the crossbars 21*b*. The design of the underside of the coupling part 2 is not limited to the design shown in FIG. 5. For example the underside can also be made as a plane solid surface.

The semi-major axis $S_{major}$ extends between the second grip means 10*a*, 10*b*, and the semi-minor axis $S_{minor}$ extends between the first grip means 9*a*,9*b*, which semi-major axis $S_{major}$ is larger than the semi-minor axis $S_{minor}$.

Figure 6:
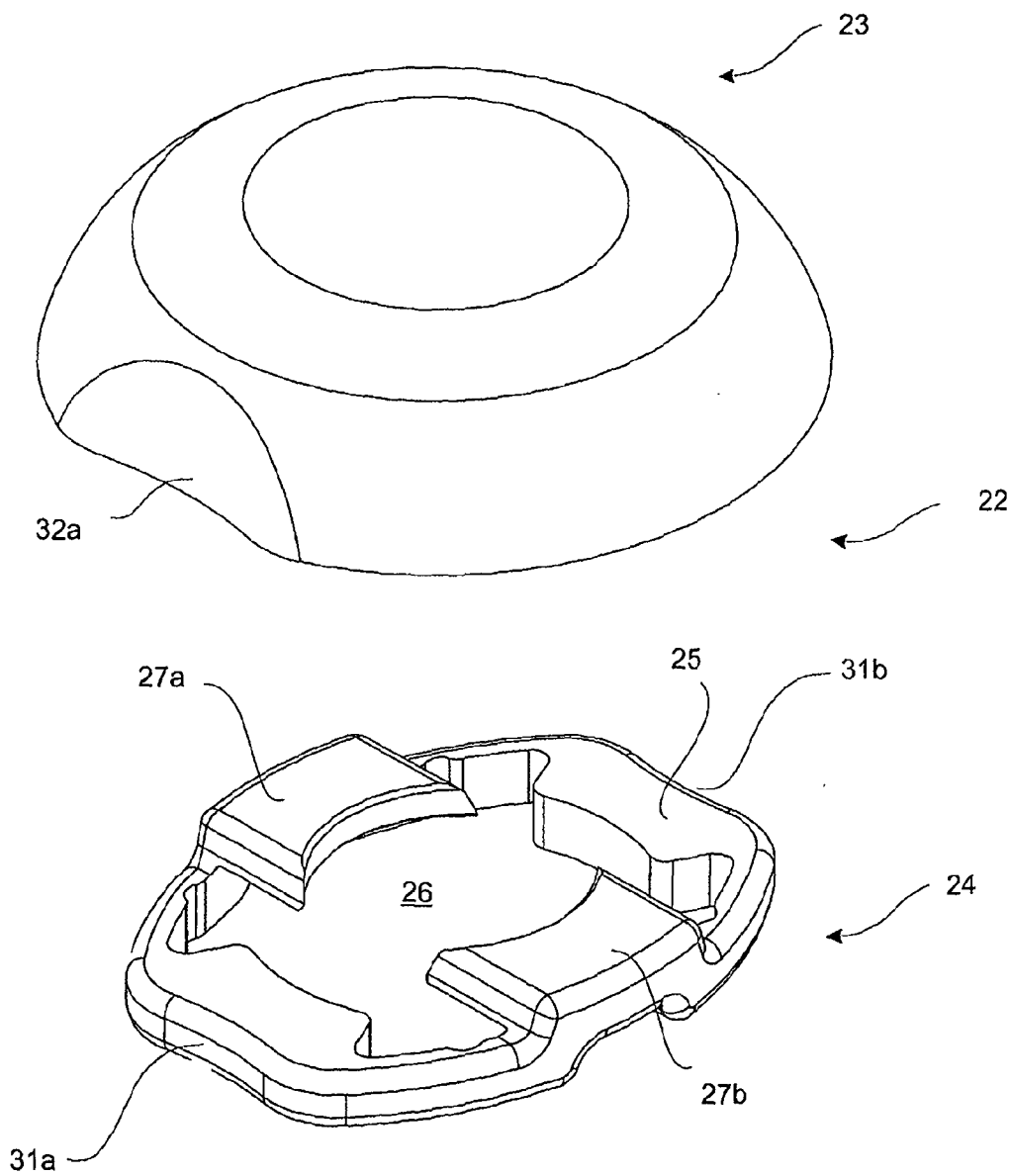
FIG. 6 shows an exploded perspective view of a second embodiment of a medical closure device for closing a discharge opening of an ostomy implant.

FIG. 6 shows an exploded perspective view of a second embodiment 22 of a medical closure device 22 for closing a discharge opening of a medical device.

The closure device 22 consists of a flexible semi-spherical closure part 23 and a flexible coupling part 24. The coupling part 24 has a circumferential flexible member 25 delimiting a coupling opening 26 and opposite projecting projections 27*a*, 27*b* facing towards each other inside the coupling opening 26 along the semi-minor axis $S_{minor}$ of the coupling part 24 and the coupling opening and above the plane of the circumferential flexible member 25.

Figure 7:
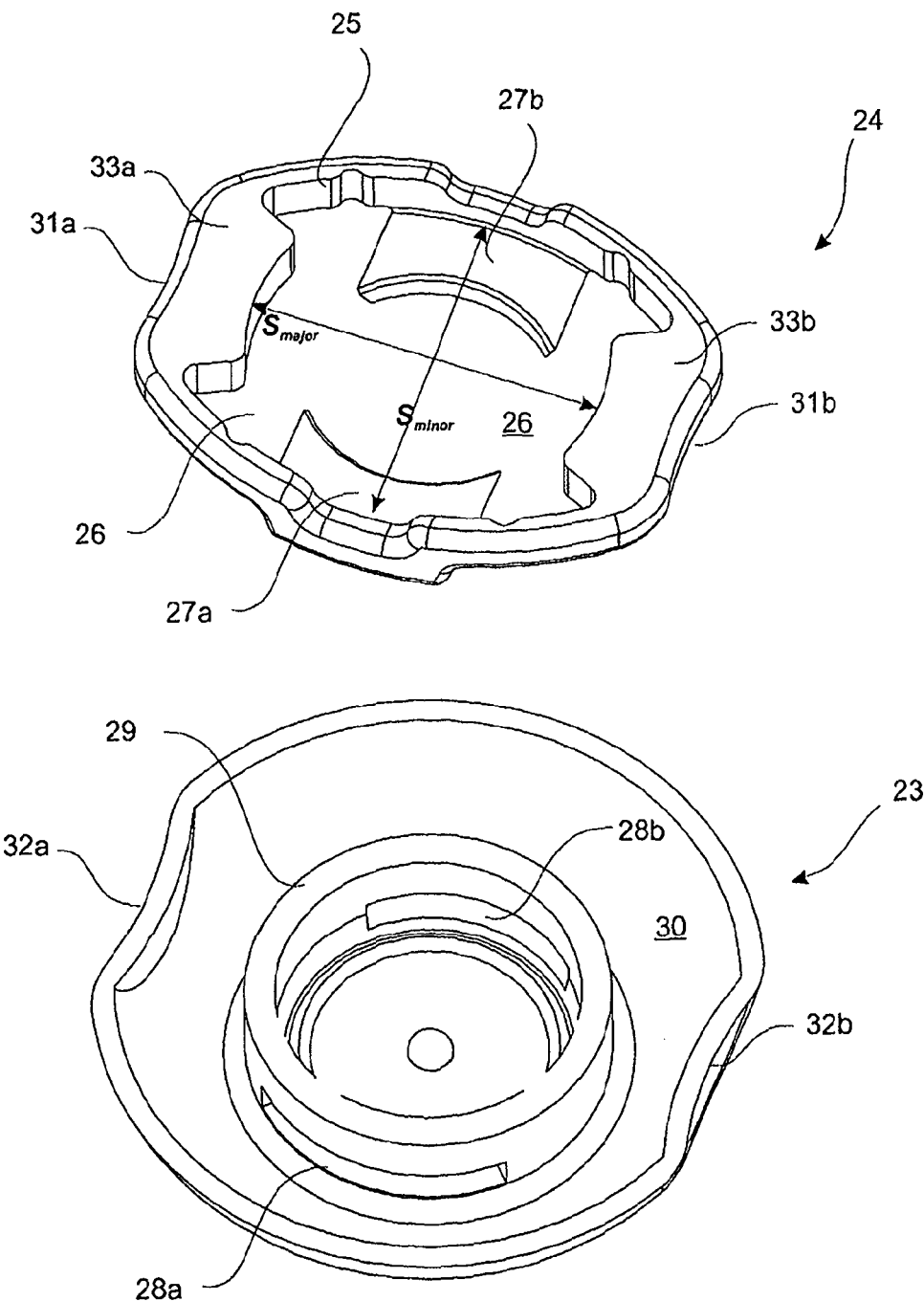
FIG. 7 shows in perspective oblique from the side facing medical device, a perspective view of the closure part and the coupling part shown in FIG. 6.
Figure 8:
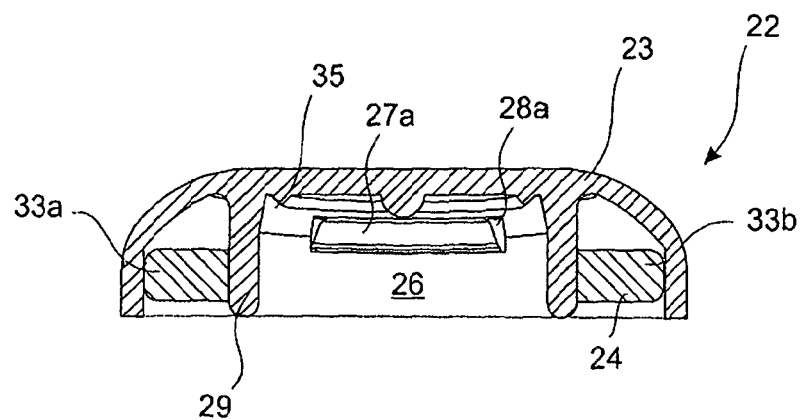
FIG. 8 is a sectional view of FIG. 8 taken through the medical closure device 22 in the assembled state.

As seen better in FIG. 7, the projections 27*a*, 27*b* are designed to mate with corresponding openings 28*a*,28*b* provided in a circumferential flange 29 protruding axially inside the cavity 30 of the semi-spherical closure part 23. The cavity 30 accommodates the coupling part 24, as seen better in the sectional view of FIG. 8 taken through the medical closure device 22 in the assembled state.

The coupling part 24 has opposite second grip means 31*a*, 31*b* along the semi-major $S_{major}$ of the coupling part 24 and the coupling opening 26, which second grip means 31*a*,31*b* is designed as indentations for easy location by the fingers. The coupling part 24 is mounted inside the cavity 30 of the closure part 23 by means of the circumferential flange 29. The closure part 23 has third grip means 32*a*,32*b* co-operative with the second grip means 31*a*,31*b* of the coupling part 22, which third grip means 32*a*,32*b* are indentations in the dome-shaped wall of the closure part 23. Accordingly, in the assembled state of the coupling part 24 and the closure part 23, the second grip means 31*a*,31*b* is located to be actuated by pressing the third grip means 32*a*,32*b* towards each other along the semi-major axis $S_{major}$ to alter the shape of the coupling opening 26, so that the coupling opening 26 allows the medical closure device 22 to be mounted on and demounted from the medical device.

In the second embodiment for a closure device 22, both the coupling part 24 and the closure part 23 are removed when access is required to the medical device. The circumferential member 25 has opposite protruding engagement members 33*a*,33*b* along the semi-major axis $S_{major}$ in the same plane as the circumferential member 25, to enhance sealing capability when mounted on the medical device.

Figure 9:
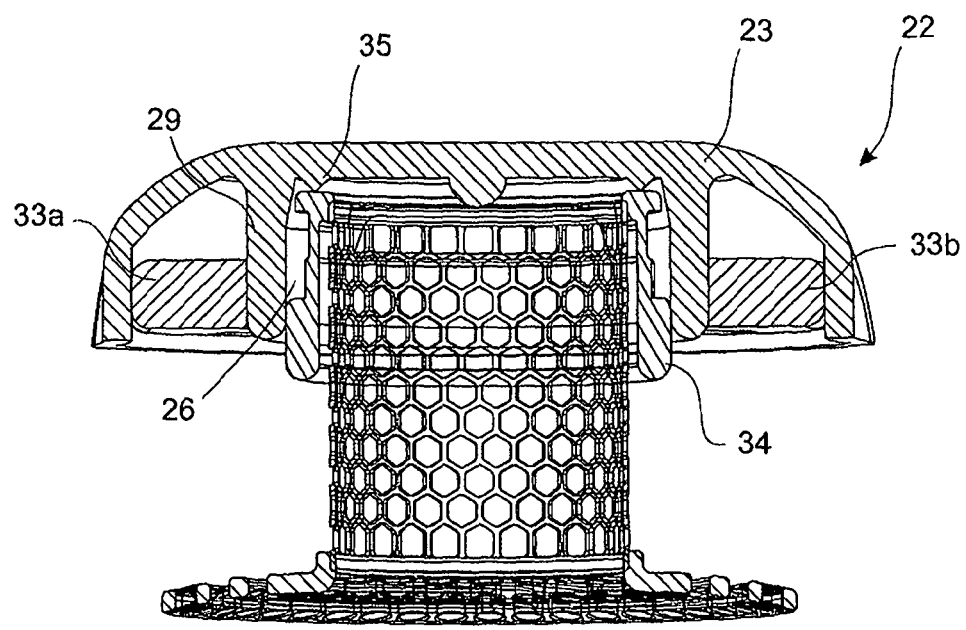
FIG. 9 shows slightly oblique from below an axial cut through the second embodiment of the closure device mounted on an ostomy implant.

An example of a medical device in the form of an implant 34 provided with the closure device 22 is seen in FIG. 9.

The circumferential flange 29 abuts the exterior tubular wall of a protruding part of the implant 34 to secure the medical closure device 22 to the implant 34. The engagement means 33*a*,33*b* of the circumferential flexible member 25 together with the circumferential flexible member 25 applies a radial force on the circumferential flange 29 to aid in keeping the medical closure device 22 firmly on the implant 34. An annular lip 35 protruding coaxially substantially concentrically with the implant 34 and the circumferential flange 29 serves as the sealing ring 35 when the closure device 22 is clamped on the implant 34. The flexibility of both closure part 23 and coupling part 24 makes the medical closure device 22 very easy to mount on the implant 34 or similar tubular part protruding from a mammalian body to seal around the implant and prevent leakage.

What is claimed is:

1. A medical closure device adapted for coupling to a discharge opening of a medical device configured to protrude from the mammalian body associated with an ostomy, which medical closure device comprises a coupling part for engaging a part of the medical device configured to protrude from the mammalian body ostomy; and
sealing means comprised in the medical device part for sealing the medical device part to the coupling part to prevent the passing from the ostomy of urine, stool or gas;
wherein the coupling part comprises a circumferential flexible member delimiting a coupling opening configurable between a relaxed configuration where the circumferential flexible member is configured and dimensioned to not allow connection of the coupling part to the sealing means of the medical device part; and
a stressed configuration where the circumferential flexible member is configured and dimensioned to provide a sealing connection of the coupling part to the sealing means of the medical device part; and
wherein the circumferential flexible member of the coupling part has a semi-minor axis radius ($S_{minor}$) that is smaller than a semi-major axis radius ($S_{major}$) in the relaxed configuration, which semi-minor axis radius ($S_{minor}$), in the relaxed configuration of the circumferential flexible member of the coupling part, prior to connecting to the sealing means of the medical device part, is smaller than an exterior radius of the sealing means of the medical device part, and
wherein the semi-minor axis radius ($S_{minor}$) of circumferential flexible member is increased in the stressed configuration to provide a sealing connection of the coupling part to the sealing means of the medical device part.

2. The medical closure device as claimed in claim 1, which is adapted to be connected to a closure part for closing the discharge opening.

3. The medical closure device as claimed in claim 1, wherein the coupling opening is substantially elliptical in the relaxed configuration.

4. The medical closure device as claimed in claim 1, wherein the coupling opening is substantially circular in the stressed configuration.

5. The medical closure device as claimed in claim 1, wherein the semi-major axis ($S_{major}$) of the coupling opening of the coupling part in the stressed configuration is
smaller than in the relaxed configuration of the coupling part,
equal to or smaller than the semi-minor axis ($S_{minor}$) the relaxed configuration of the coupling part, or
smaller than the semi-minor axis ($S_{major}$) in the stressed configuration of the coupling part.

6. The medical closure device as claimed in claim 1, wherein the coupling part has engagement means for engaging the medical device part, or securing means for securing the coupling part to a closure part, or both means.

7. A medical closure device adapted for coupling to a discharge opening of a medical device configured to protrude from the mammalian body associated with an ostomy, which medical closure device comprises:
a coupling part adapted for engaging a part of the medical device configured to protrude from the mammalian body ostomy, wherein the coupling part comprises a circumferential flexible member delimiting a coupling opening configurable between a relaxed configuration where the circumferential flexible member is configured and dimensioned to not allow connection of the coupling part to a sealing means of the medical device part; and
a stressed configuration where the circumferential flexible member is configured and dimensioned to provide a sealing connection of the coupling part to the sealing means of the medical device part, and
wherein the sealing means is comprised in the medical device part for sealing the medical device part to the coupling part to prevent the passing from the ostomy of urine, stool or gas; and
wherein the sealing means is comprised in the medial device part for sealing the medical device part to the coupling part to prevent the passing from the ostomy of urine, stool or gas; and
wherein the circumferential flexible member of the coupling part has a semi-minor axis radius ($S_{minor}$) that is smaller than a semi-major axis radius ($S_{major}$) in the relaxed configuration, which semi-minor axis radius ($S_{minor}$), in the relaxed configuration of the circumferential flexible member, prior to connecting the sealing means of the medical device part, is smaller than an exterior radius of the sealing means of the medical device part, and
wherein the semi-minor axis radius ($S_{minor}$) of circumferential flexible member is increased in the stressed configuration to provide a sealing connection of the coupling part to the sealing means of the medical device part.

8. The medical closure device as claimed in claim 7, wherein the sealing means comprises a sealing ring.

9. The medical closure device as claimed in claim 7, wherein the sealing means comprises a sealing disc.

10. The medical closure device as claimed in claim 1, wherein the circumferential flexible member forming the coupling part has at least one aperture, through-opening or cut-out.

11. The medical closure device as claimed in claim 6, wherein the coupling part has first grip means for at least operating the coupling part during attachment to and detachment from the closure part, second grip means for at least gripping the coupling part during configuration of the coupling opening between the relaxed configuration and the stressed configuration and vice versa, or both grip means.

12. The medical closure device as claimed in claim 11, wherein the first grip means is arranged along the semi-minor axis ($S_{minor}$) and the second grip means is arranged along the semi-major axis.

13. The medical closure device as claimed in claim 6, wherein the closure part is provided with third grip means for gripping the closure part during attachment and detachment of the closure part and the coupling part.

14. The medical closure device as claimed in claim 6, wherein the closure part has a concavity for accommodating at least a part of the coupling part and a part of the medical device part that is configured to protrude from the mammalian body.

15. The medical closure device as claimed in claim 6, wherein at least one of the coupling part or the closure part is made of a flexible material having memory shape, or has memory shape due to structural design.

16. The medical closure device as claimed in claim 1, wherein the closure part is a cap, an ostomy bag, a catheter, or an irrigation device.

17. A method for application of a medical closure device onto a medical device part configured to protrude from a mammalian body associated with an ostomy, the method comprising:
   providing the medical closure device comprising a coupling part for engaging a medical device part of the medical device configured to protrude from the mammalian body ostomy, wherein the coupling part comprises a circumferential flexible member delimiting a coupling opening, the circumferential flexible member having a semi-minor axis radius ($S_{minor}$) that is smaller than a semi-major axis radius ($S_{major}$) in a relaxed configuration, which semi-minor axis radius ($S_{minor}$), in the relaxed configuration of the circumferential flexible member, prior to connecting to a sealing means of the medical device part, is smaller than an exterior radius of the sealing means of the medical device part,
   wherein the circumferential flexible member is configurable between:
      the relaxed configuration where the circumferential flexible member is configured and dimensioned to not allow connection of the coupling part to the sealing means of the medical device part; and
      a stressed configuration where the circumferential flexible member of the coupling part is configured and dimensioned to provide a sealing connection of the coupling part to the sealing means of the medical device part;
   increasing the length of the semi-minor axis ($S_{minor}$) by applying an exterior force to the circumferential flexible member of the coupling part to allow the circumferential flexible member to align with the sealing means of the medical device part,
   arranging the circumferential flexible member of the coupling part to surround the sealing means of the medical device part,
   relaxing the exterior force allowing the circumferential flexible member of the coupling part to form the stressed configuration, and
   thereby providing a sealing connection between the closure device and the medical device to prevent the passing from the ostomy of urine, stool or gas;
   wherein the semi-minor axis radius ($S_{minor}$) of circumferential flexible member is increased in the stressed configuration to provide a sealing connection of the coupling part to the sealing means of the medical device part.

18. The method as claimed in claim 17, wherein the coupling part and the closure part are screwed together or snap-fitted together.

19. The method as claimed in claim 17, wherein the medical device is an ostomy implant or other medical implant.

20. A closure part adapted for mounting to a medical closure device as claimed in claim 1.

21. The closure part as claimed in 20, further comprising securing means for securing the closure part to the coupling part of the medical closure device.

22. A kit comprising a medical closure device as claimed in claim 1 and a closure part adapted for mounting to the medical closure device for closing the medical closure device.

23. A method of coupling a medical closure device to a discharge opening of a medical device part configured to protrude from a mammalian body ostomy, the method comprising:
   providing the medical closure device comprising a sealing means of a coupling part for engaging a sealing means of the medical device part configured to protrude from the mammalian body ostomy, wherein the coupling part comprises a circumferential flexible member delimiting a coupling opening;
   applying force to the circumferential flexible member of the coupling part in a relaxed configuration wherein the circumferential flexible member of the coupling part is configured and dimensioned to not allow connection onto the sealing means of the medical device part, with the applied force placing the circumferential flexible member of the coupling part in a stressed configuration wherein it is configured and dimensioned to receive the sealing means of the medical device part;
   locating the coupling opening of the circumferential flexible member in the stressed configuration around the sealing means of the medical device part; and
   relaxing the force on the circumferential flexible member of coupling part so that it at least partially returns to the relaxed configuration, whereby the medical closure device becomes attached to the medical device part configured to protrude from the mammalian body;
   wherein the coupling opening of the circumferential flexible member of the coupling part has a semi-minor axis ($S_{minor}$) that is smaller than a semi-major axis ($S_{major}$) in the relaxed configuration, which semi-minor axis ($S_{minor}$), in the relaxed configuration of the circumferential flexible member of the coupling part, prior to connecting the coupling opening of the circumferential flexible member to the sealing means of the medical device part, is smaller than an exterior radius of the sealing means of the medical device part to be surrounded by the circumferential flexible member of the coupling part;
   thereby providing a sealing connection between the closure device and the medical device to prevent the passing from the ostomy of urine, stool or gas;
   wherein the semi-minor axis radius ($S_{minor}$) of circumferential flexible member is increased in the stressed configuration to provide a sealing connection of the coupling part to the sealing means of the medical device part.

24. The method as claimed in 23, wherein in the relaxed configuration the coupling opening is substantially elliptical.

25. The method as claimed in 24, wherein in the stressed configuration the coupling opening is less elliptical than in the relaxed configuration.

26. The method as claimed in 23, wherein in the stressed configuration the coupling opening is substantially circular.

27. A medical closure device as claimed in claim 1, wherein the coupling part is deformable between the relaxed configuration and the stressed configuration by the application of pressure to the coupling part.

28. The medical closure device as claimed in claim 27, wherein the coupling part is deformable between the relaxed configuration and the stressed configuration by the application of pressure on opposite sides of the coupling part.

29. The medical closure device as claimed in claim 27, wherein the coupling part is arranged such that upon release of pressure, the coupling part at least partially returns to the relaxed configuration.

30. The medical closure device as claimed in claim 13, wherein the closure part, the coupling part and the medical device part include means for screwing or unscrewing, snap-fitting or snap-fastening or reversing the snap-fitting or the snap-fastening of such parts and the and the gripping means facilitates such operations.

* * * * *

UNITED STATES PATENT AND TRADEMARK OFFICE
CERTIFICATE OF CORRECTION

PATENT NO. : 9,107,764 B2  
APPLICATION NO. : 13/499621  
DATED : August 18, 2015  
INVENTOR(S) : Jacobsson et al.

It is certified that error appears in the above-identified patent and that said Letters Patent is hereby corrected as shown below:

<u>Title Page:</u>
Item (75) Inventors, after "Jens Nygarden", delete "Brandstorm" and insert -- Brandstrom --.
The inventor's name will then correctly appear as "Jens Nygarden Brandstrom".

Signed and Sealed this
Twenty-second Day of December, 2015

Michelle K. Lee
*Director of the United States Patent and Trademark Office*